US009775510B2

(12) United States Patent
Knighton et al.

(10) Patent No.: US 9,775,510 B2
(45) Date of Patent: Oct. 3, 2017

(54) METHODS TO REDUCE VARIANCE IN OCT ANALYSIS OF THE MACULA

(71) Applicant: Carl Zeiss Meditec, Inc., Dublin, CA (US)

(72) Inventors: Robert W. Knighton, Duluth, MN (US); Matthew J. Everett, Livermore, CA (US); Mary K. Durbin, San Francisco, CA (US); Jonathan D. Oakley, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 426 days.

(21) Appl. No.: 14/316,548

(22) Filed: Jun. 26, 2014

(65) Prior Publication Data

US 2014/0307933 A1 Oct. 16, 2014

Related U.S. Application Data

(62) Division of application No. 13/250,699, filed on Sep. 30, 2011, now Pat. No. 8,801,187.

(Continued)

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *G06T 7/0012* (2013.01); *G06T 7/12* (2017.01);
(Continued)

(58) Field of Classification Search
CPC ....... A61B 3/10; A61B 3/1005; A61B 3/1015; A61B 3/102; A61B 3/113; A61B 3/12;
(Continued)

(56) References Cited

U.S. PATENT DOCUMENTS 7,347,548 B2  3/2008  Huang et al.
7,641,339 B2  1/2010  Hangai et al.
(Continued)

OTHER PUBLICATIONS

Non-Final Office Action received for U.S. Appl. No. 13/250,699, mailed on Sep. 12, 2013, 15 pages.
(Continued)

*Primary Examiner* — Ricky Mack
*Assistant Examiner* — Robert E Tallman
(74) *Attorney, Agent, or Firm* — Morrison & Foerster LLP

(57) ABSTRACT

Methods for analyzing optical coherence tomography (OCT) images of the macula to reduce variance and improve disease diagnosis are presented. One embodiment of the invention is directed towards selecting analysis locations and data segmentation techniques to take advantage of structural homogeneities. Another embodiment is directed towards reducing the variance in a collection of normative data by transforming the individual members of the database to correspond to a Standard Macula. Variations in foveal size are corrected by radial transformation. Variations in layer thickness are corrected by axial shifting. Diagnosis is performed by comparing OCT images from a patient to the improved normative database.

12 Claims, 14 Drawing Sheets

Related U.S. Application Data

(60) Provisional application No. 61/427,006, filed on Dec. 23, 2010.

(51) Int. Cl.
| | | |
|---|---|---|
| *G06T 7/00* | (2017.01) | |
| *G06T 7/60* | (2017.01) | |
| *G06T 7/12* | (2017.01) | |
| *G06T 7/162* | (2017.01) | |

(52) U.S. Cl.
CPC ............ *G06T 7/162* (2017.01); *G06T 7/60* (2013.01); *G06T 2207/10101* (2013.01); *G06T 2207/30041* (2013.01)

(58) Field of Classification Search
CPC ....... A61B 3/1225; G06T 7/00; G06T 7/0002; G06T 7/0012; G06T 7/0014; G06T 7/0083
USPC ............... 351/200, 205, 206, 208, 209, 210
See application file for complete search history.

(56) References Cited

U.S. PATENT DOCUMENTS

| | | |
|---|---|---|
| 7,798,647 B2 | 9/2010 | Meyer et al. |
| 8,025,407 B2 | 9/2011 | Huang et al. |
| 8,474,978 B2 | 7/2013 | Huang et al. |
| 2008/0309881 A1 | 12/2008 | Huang et al. |
| 2009/0033868 A1* | 2/2009 | Huang ............... A61B 3/1005 351/205 |
| 2010/0277691 A1 | 11/2010 | Huang et al. |
| 2010/0290004 A1 | 11/2010 | Huang et al. |
| 2010/0290005 A1 | 11/2010 | Huang et al. |
| 2011/0267340 A1* | 11/2011 | Kraus ................ A61B 3/102 345/419 |

OTHER PUBLICATIONS

Notice of Allowance received for U.S. Appl. No. 13/250,699, mailed on Mar. 26, 2014, 8 pages.
Choma et al., "Sensitivity Advantage of Swept Source and Fourier Domain Optical Coherence Tomography", Optics Express, vol. 11, No. 18, Sep. 8,2003, pp. 2183-2189.
Fernandez et al., "Automated Detection of Retinal Layer Structures on Optical Coherence Tomography Images", Optics Express, vol. 13, No. 25, Dec. 12, 2005, pp. 10200-10216.
Gregori et al., "The Geometry of the Normal Fovea", Investigative Ophthalmology & Visual Science, vol. 51, The Association for Research in Vision and Ophthalmology Program, Poster #D623, 2010, (E-Abstract) 2 pages.
Gurses-Ozden et al., "Distribution of Retinal Nerve Fiber Layer Thickness Using CirrusTM HD-OCT Spectral Domain Technology", Invest Ophthalmol Vis Sci, vol. 49, Poster #A258, 2008, (E-Abstract), 2 pages.
Haeker et al., "Use of Varying Constraints in Optimal 3-D Graph Search for Segmentation of Macular Optical Coherence Tomography Images", Med Image Comput Comput Assist Interv, vol. 10, part-1, 2007, pp. 244-251.
Ishikawa et al., "Macular Segmentation with Optical Coherence Tomography", Investigative Ophthalmology & Visual Science, vol. 46, No. 6, Jun. 2005, pp. 2012-2017.
Kotera et al., "Three-Dimensional Imaging of Macular Inner Structures in Glaucoma by Using Spectral-Domain Optical Coherence Tomography", Investigative Ophthalmology & Visual Science, vol. 52, No. 3, Mar. 2011, pp. 1412-1421.
Leung et al., "Comparison of Macular and Peripapillary Measurements for the Detection of Glaucoma : An Optical Coherence Tomography Study", Ophthalmology, vol. 112, No. 3, Mar. 2005, pp. 391-400.
Loduca et al., "Thickness Mapping of Retinal Layers by Spectral-Domain Optical Coherence Tomography", American Journal of Ophthalmology, vol. 150, No. 6, Dec. 2010, pp. 849-855.
Mwanza et al., "Macular Ganglion Cell—Inner Plexiform Layer: Automated Detection and Thickness Reproducibility with Spectral Domain—Optical Coherence Tomography in Glaucoma", Investigative Ophthalmology & Visual Science, vol. 52, No. 11, Oct. 2011, pp. 8323-8329.
Mwanza et al., "Profile and Predictors of Normal Ganglion Cell—Inner Plexiform Layer Thickness Measured with Frequency-Domain Optical Coherence Tomography", Investigative Ophthalmology & Visual Science, vol. 52, No. 11, Oct. 2011, pp. 7872-7879.
Nakano et al., "Macular Ganglion Cell Layer Imaging in Preperimetric Glaucoma with Speckle Noise-Reduced Spectral Domain Optical Coherence Tomography", Ophthalmology, vol. 118, No. 12, Dec. 2011, pp. 2414-2426.
Ooto et al., "Effects of Age, Sex, and Axial Length on the Three-Dimensional Profile of Normal Macular Layer Structures", Investigative Ophthalmology & Visual Science, vol. 52, No. 12, Nov. 2011, pp. 8769-8779.
Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.e2.
Tan et al., "Measurement of Ganglion Cell Layer and Inner Plexiform Layer Thickness with Optical Coherence Tomography", Investigative Ophthalmology & Visual Science, vol. 44, The Association for Research in Vision and Ophthalmology Program# B585, 2003, (E-Abstract) 2 pages.
Wagner-Schuman et al., "Race- and Sex-Related Differences in Retinal Thickness and Foveal Pit Morphology", Investigative Ophthalmology & Visual Science, vol. 52, No. 1, Jan. 2011, pp. 625-634.
Wang et al., "Measurement of Local Retinal Ganglion Cell Layer Thickness in Patients With Glaucoma Using Frequency-Domain Optical Coherence Tomography", Arch Ophthalmol, vol. 127, No. 7, Jul. 2009, pp. 875-881.
Yang et al., "Automated Layer Segmentation of Macular OCT Images Using Dual-Scale Gradient Information", Optics Express, vol. 18, No. 20, Sep. 27, 2010, pp. 21293-21307.
Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul. / Aug. 2007, pp. 041206-1-041206-8.

\* cited by examiner

METHODS TO REDUCE VARIANCE IN OCT ANALYSIS OF THE MACULA

PRIORITY

This application is a divisional of U.S. Ser. No. 13/250,699, filed Sep. 30, 2011, which in turn claimed priority to U.S. Provisional Application Ser. No. 61/427,006, filed Dec. 23, 2010, the entire disclosures of which are incorporated by reference.

TECHNICAL FIELD

One or more embodiments of the present invention relate generally to evaluation of the macular region of the eye. In particular the invention described herein provides a means to reduce the variance of optical coherence tomography measurements collected over this region to provide more specific and sensitive disease diagnosis and progression analysis.

BACKGROUND

Glaucoma is a term used to describe a group of diseases characterized by the loss of retinal ganglion cells and their axons and is one of the leading causes of blindness in the world. In many cases, vision loss due to glaucoma is irreversible. Glaucoma diagnosis is most commonly associated with an increase in intraocular pressure (IOP); however, diagnosis may also be based on the assessment of the optic nerve head (ONH), visual function, and/or the health and thickness of the retinal nerve fiber layer (RNFL). Methods of OCT glaucoma analysis have been based primarily on a scan pattern centered at the optic nerve head (ONH), where the ganglion cell axons (or retinal nerve fiber layer—RNFL) converge to exit the eye. Structural measurements that are clinically relevant to the disease include measurements of the thickness of the RNFL in the peripapillary region as well as measurements of characteristics of the optic nerve head such as 'cupping'. Both of these methods have been developed commercially (Carl Zeiss Meditec Cirrus version 5.1 software) and are accepted as good structural indicators of disease status. The scan pattern used for both measurements is the Optic Disc Cube, which is 200-by-200 A-scans, covering a 6 mm-by-6 mm lateral area, and 2 mm axial depth.

As measured, the RNFL or ganglion cell axons are perhaps the gold-standard, automated structural measurement for glaucoma management. It is not clear whether it is the axons or the cells themselves that die first in glaucoma. The ganglion cell bodies are distributed throughout the eye, but have the greatest density around the fovea and receive electrical signals from the photoreceptors (the rods and cone cells). These signals are then organized and passed onward through the RNFL via the optic nerve head to the brain's lateral geniculate body for further processing before being sent to the visual cortex. The ganglion cell bodies form the ganglion cell layer (GCL), which, it is hypothesized, might show the earliest signs of glaucomatous damage. (See Leung et al., "Comparison of macular and peripapillary measurements for the detection of glaucoma: an optical coherence tomography study" *Ophthalmology* 2005 March; 112(3): 391-400.)

FIG. 1 shows the various layers at the macula. The anterior boundary of the GCL is the posterior boundary of the RNFL, or the ILM where no RNFL exists. It can be seen that the GCL's posterior boundary is very faint, which may be in part an answer as to why the RNFL is instead measured in current instruments; i.e., it can more easily be seen and measured. In fast, volumetric scans about the macula, the GCL can be seen in only the minority of cases. This, in turn, has led researchers to segment a so-called ganglion cell complex (GCC). That is, they include additional, surrounding layers with the objective of making the GCC a measurable entity. One such segmentation is available commercially from Optovue, where the GCC is defined as the RNFL+GCL+IPL (see U.S. Patent Publication No. 2008/0309881). The segmentation task is still non-trivial, and that is probably why the metric has yet to be proven to be better than the gold standard of peripapillary RNFL thickness with respect to efficacy in detecting disease.

FIG. 2 shows a reason to avoid including the RNFL in the ganglion cell complex. The top row of the figure shows thickness maps or images derived from macular scans of four normal subjects, segmented to identify the thickness of the ganglion cell complex including the RNFL, ganglion cell and inner plexiform layers. The bottom row shows maps from the same scans, segmenting only the GCL and the IPL. The distribution of RNFL varies as a result of an individual's anatomy, and it is possible that this variability exceeds the variation due to glaucoma (see Ozden-Gurses et al., "Distribution of retinal nerve fiber layer thicknesses using Cirrus™HD–OCT Spectral Domain technology" *ARVO* 2008 Program #A258, Poster #4632). A characterization that does not include the RNFL layer may present a topographically more homogeneous base from which to visualize defects and damage due to the presence of disease, and thereby provide a better means to detect and track glaucoma progression. Spectral-domain OCT has been demonstrated to measure the thickness of the ganglion cell and inner plexiform layers combined. (See, Loduca et al. "Thickness mapping of retinal layers by spectral-domain optical coherence tomography" *Am J Ophthalmol* 2010; 150(6): 849-855; or Wang et al. "Measurement of local retinal ganglion cell layer thickness in patients with glaucoma using frequency-domain optical coherence tomography" *Arch Ophthalmol* 2009; 127(7): 875-881.)

Comparison of measurements to normative data is a common procedure for analyzing the health of a patient's eye. The anatomy of the ONH has considerable interindividual variability; it varies in size and shape, in the degree of tilt relative to the back of the eye and in the configuration of the large blood vessels that run through its center. These variations prevent accurate characterization of the ONH in a simple form that can be compared across individuals. The anatomy of the RNFL also has considerable interindividual variability. Bundles of ganglion cell axons, although they converge toward the ONH in a more-or-less radial pattern, do so along various paths, some more arcuate, some less, and sometimes with inferior or superior bifurcations. Thus the so-called TSNIT pattern (circular profile) of the peripapillary RNFL can be double or triple humped, with varying separation between the maxima. These variations decrease the diagnostic accuracy of comparisons to normative data in these regions (see for example U.S. Pat. No. 7,798,647 hereby incorporated by reference).

In contrast to the ONH and RNFL, the topographical homogeneity of the normal macular GCL+IPL apparent in FIG. 2 permits a characterization of the GCL or GCL+IPL as a canonical form, that is, as a standard way of presenting these layers. Such a canonical form can be regarded as a Standard Macula. FIG. 2 suggests that for the GCL or GCL+IPL, the Standard Macula has approximately the shape of a thickened elliptical annulus. Thus, although the GCL or GCL+IPL of normal maculas may vary in size, shape and thickness, all can be described by properties of a Standard Macula following suitable spatial transformation. Similarly, transformations applied to a Standard Macula permit comparison to the GCL or GCL+IPL of a patient's eye as a means of diagnosis.

Based on the above discussion, it is an object of the present invention to develop a method to characterize the thickness of layers of the macula in an effort to best discriminate normal from glaucomatous eyes and detect changes due to glaucoma over time. It is a further object of the invention to develop a means to compare this characterization to normative data with a reduced variance due to anatomical variations.

DETAILED DESCRIPTION

The invention described herein is directed towards providing reduced variance in the indication of disease state in the eye of a patient. This is accomplished either by selecting the region or regions for analysis with the greatest topographical homogeneity or the least amount of interindividual variability or by accounting for or reducing the interindividual variability in the collection of measurements from a normal population prior to analysis.

The method herein is focused on a combination of the ganglion cell and inner plexiform layers (GCL+IPL) but could also be applied to the ganglion cell layer on its own or to other layers or combinations of layers within the macula. As described above, the ganglion cell layer (GCL), is the preferred tissue layer for diagnosing and following glaucoma, but the GCL+IPL is dominated by the GCL as it approaches the foveal slope so is almost equivalent to the GCL over the macular region. The normal configuration of the macular GCL is a nearly elliptical annulus 6-8 ganglion cell bodies thick surrounding the fovea. Ganglion cells are absent in the foveal center and the GCL declines to a layer of single cell bodies in the periphery. Ganglion cells send their axons to the ONH in the RNFL in a pattern that divides between superior and inferior retina along a line temporal to the fovea called the temporal raphe. The chief sources of interindividual variability of the macular GCL are the size and thickness of the perifoveal annulus. This simple topography allows the use of a canonical form, that is, a standard way of presenting an object, to describe the normal macular GCL.

The present invention provides methods for generating and analyzing two-dimensional maps or images of three dimensional measurement data collected in the macular region of the eye using non-invasive imaging techniques such as optical coherence tomography (OCT) which includes both time domain and frequency domain systems. Such an instrument generates 3D intensity data corresponding to an axial reflection distribution arising from reflecting features in the eye. This information is used by doctors to view and diagnosis various pathologies in the eye.

Figure 1:
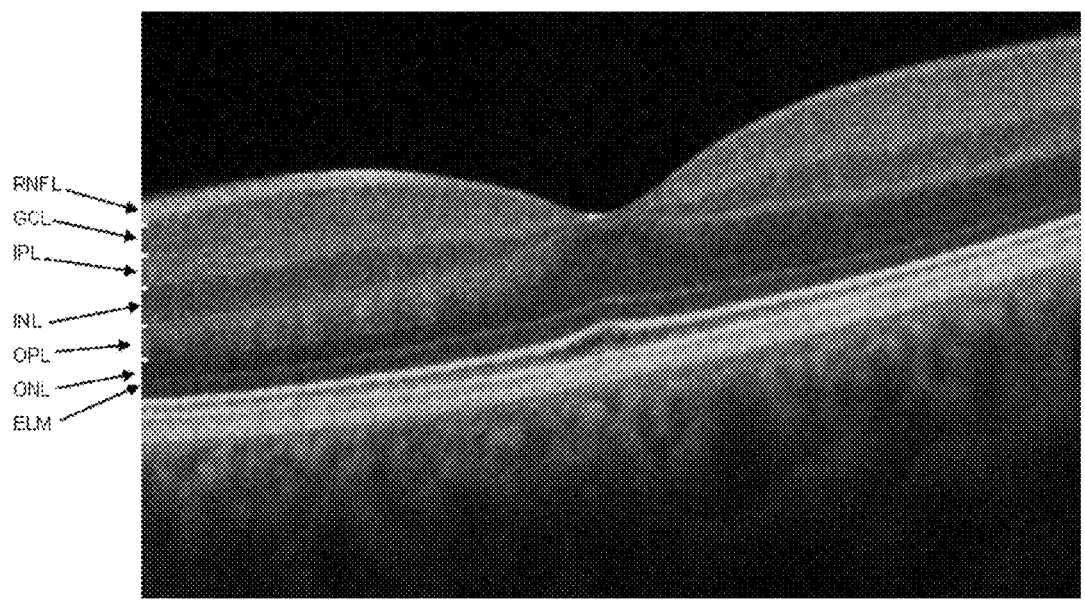
FIG. 1 shows the various layers at the macula
Figure 2:
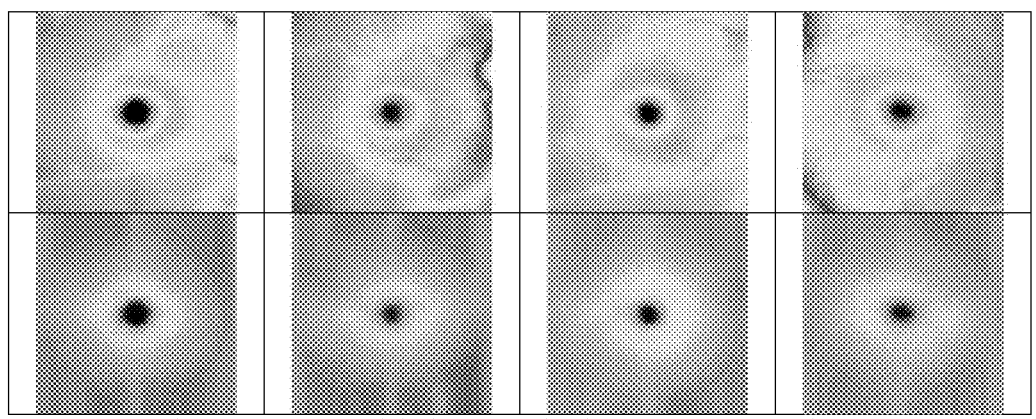
FIG. 2 shows thickness maps of the RNFL+GCL+IPL (top 4 images) and GCL+IPL (bottom 4 images) for four normal subjects.
Figure 3:
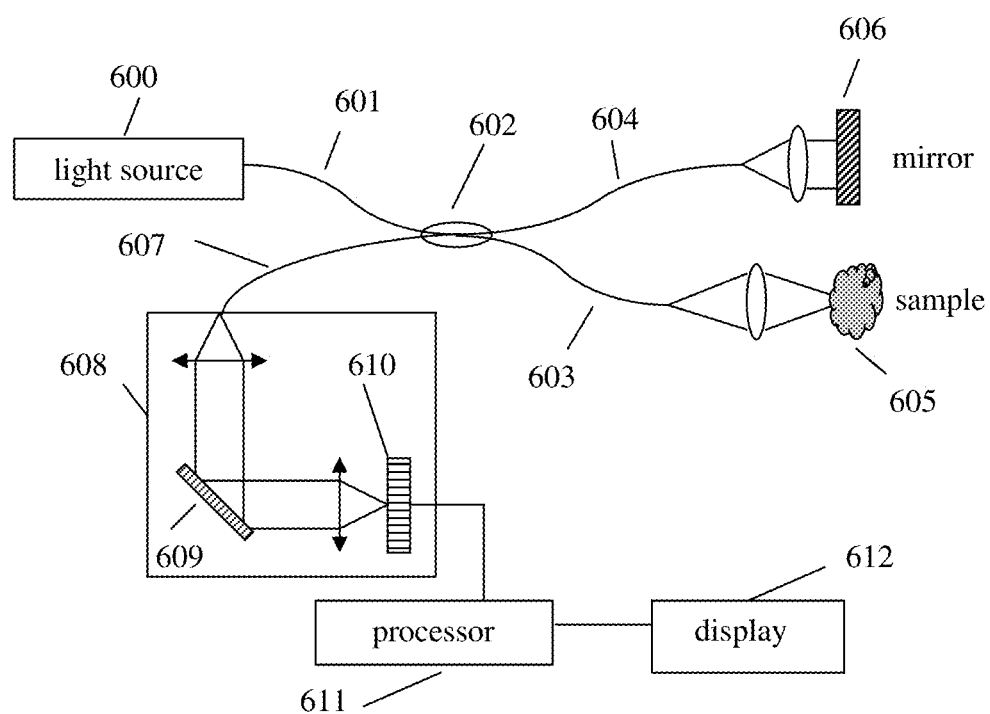
FIG. 3 shows a block diagram of a spectrometer based SD-OCT system.

The example described herein uses spectral domain OCT (SD-OCT). A basic block diagram for a spectrometer based spectral domain OCT system is shown in FIG. 3. The light source 600 provides broad bandwidth light to a short length of an optical fiber 601 to an input port of a fiber optic coupler 602, which splits the incoming light beam into the two arms of an interferometer. The two arms each have a section of optical fiber 603 and 604 that guides the split light beam from the fiber coupler 602 to a sample 605 and a reference reflector 606 respectively. For both the sample arm and the reference arm, at the terminating portion of each fiber, there may be a module containing optical elements to collimate or focus or scan the beam. The returned light waves from the sample 605 and the reference reflector 606 are directed back through the same optical path of the sample and reference arms and are combined in fiber coupler 602. A portion of the combined light beam is directed through a section of optical fiber 607 from the fiber coupler 602 to a spectrometer 608. Inside the spectrometer, the light beam is dispersed by a grating 609 and focused onto a detector array 610. The collected data is sent to a processor 611 and the resulting processed data can be displayed on a display 612 or stored in memory for future reference. Note that the principle of operation of a tunable laser based swept source OCT is very similar to that of a spectrometer based spectral domain OCT system (see for example, Choma, M. A. et al. (2003)). "Sensitivity advantage of swept source and Fourier domain optical coherence tomography". Optics Express 11(18): 2183-2189), hence the spectral domain OCT system for obtaining the 3D image data set can also be a swept source OCT system.

This example case will be based on the use of SD-OCT; in particular, based on a cube of 200-by-200-by-1024 voxels, that corresponds to a volume of 6 mm-by-6 mm-by-2 mm in the retina, but other scan sizes including 512×128 could also be used. The axial direction here is along the path of the beam of light that enters the eye and covers a depth of 2 mm. SD-OCT has a very fast acquisition rate, enabling true volumetric images to be collected in a very short time, maximizing routine clinical utility. For example, a volume of 200-by-200-by-1024 voxels covering a field-of-view (FOV) of 6-by-6-by-2 mm in the eye can be collected in ~1.6 seconds using commercially available instruments. Applying image processing algorithms to such data allows for automatic measurements of structure in the image, where the target measurements pertain, typically, to disease staging.

Once obtained the 3D intensity data can be segmented to identify various layers and layer boundaries. For instance, Tan et al describe using an iterative method based on gradients of reflectivity between layers (Tan et al., "Detection of Macular Ganglion Cell Loss in Glaucoma by Fourier-Domain Optical Coherence Tomography," *Ophthalmology* 2009; 116(12)). Such methods depend on signal detected independently in each A-scan.

For three dimensional data, additional accuracy and repeatability can be obtained by including information from neighboring pixels, and by including information known about the expected layer architecture. Haeker et al., describe a graph-search method with varying constraints that allows the algorithm to be trained to expected layer smoothness constraints and expected separation distances between layers (Haeker et al., "Use of Varying Constraints in Optimal 3-D Graph Search for Segmentation of Macular optical Coherence Tomography Images," *MICCAI* 2007 *Presentation* 438). Another method that utilizes neighboring information is a Support Vector Machine based segmentation, described by Zawadzki et al. (Zawadzki et al., "Adaptation of a support vector machine algorithm for segmentation and visualization of retinal structures in volumetric optical coherence tomography data sets," *J Biomed Opt.* 2007 ; 12(4)). This method allows information about expected retinal structures to be input. Both of these methods require clinical input at some level—for the graph search method a training set is segmented by the user, while for the SVM method the user must select reference points located in specific layers on each image to be segmented.

We propose that using a priori knowledge of the retinal architecture can improve segmentation performance. The ganglion cell and retinal nerve fiber layers both are reduced to zero or near zero at the fovea. Thus, if the fovea can be identified, it becomes an excellent seed point for setting constraints required by the graph search method. Note that the graph search method can also be implemented in a manner that takes advantage of the polar coordinates described later in this document, while still allowing inclusion of neighboring information in the cost function that determines the layer assignment.

Additional information about the architecture of layers in the vicinity of the fovea includes the fact that for normal eyes, the cone density at and near the fovea is significantly higher than rod density, and cones are longer than rods. This leads to a characteristically raised appearance of the reflective layer that represents the boundary between the inner segments and outer segments of the photoreceptors. This can be used in identifying the fovea, or in a layer segmentation aimed at detecting the photoreceptors. It is also possible that the rate of change of the ganglion cell or retinal nerve fiber layers, from zero thickness at the fovea to their full thickness in the perifoveal region for the GCL and in the optic disc region for the RNFL, depends on the distance from the fovea to the optic disc or on the length of the eye. These characteristics could be used to create a model of the layers in the eye and their distribution to which the observed layer thickness values could be compared.

In the preferred embodiment, the segmentation algorithm requires the inner-limiting membrane (ILM) and retinal pigment epithelial (RPE) boundaries as input as well as the location of the fovea. These segmentations have been commercially available in Cirrus since version 2.0, and are widely accepted as reliable and accurate. In this preferred embodiment (described in Mwanza et al "Macular Ganglion Cell-Inner Plexiform Layer: Automated Detection and Thickness Reproducibility with Spectral-Domain Optical Coherence Tomography" IOVS Manuscript iovs. 11-7692 hereby incorporated by reference), the algorithm operates in a hierarchical approach segmenting first the outer boundary of the outer plexiform layer (OPL), followed by the outer boundary of the inner plexiform layer (IPL), and lastly the outer boundary of the RNFL. The segmentation procedure operates entirely in three dimensions and uses a graph-based algorithm to identify each layer. The image data is transformed into cost images such that the graph algorithm can find the lowest cost surface. To do this, the input data is initially median filtered to reduce speckle noise. It then creates cost images based on directional edge filtered images that have been additionally enhanced to highlight specific boundary intensity changes using a sigmoid function. These are additionally combined with positional cost images to form a single representation that is partitioned by the graph segmentation algorithm. The segmentation that results is globally optimal in terms of its cumulative cost for each of the layers.

Figure 4:
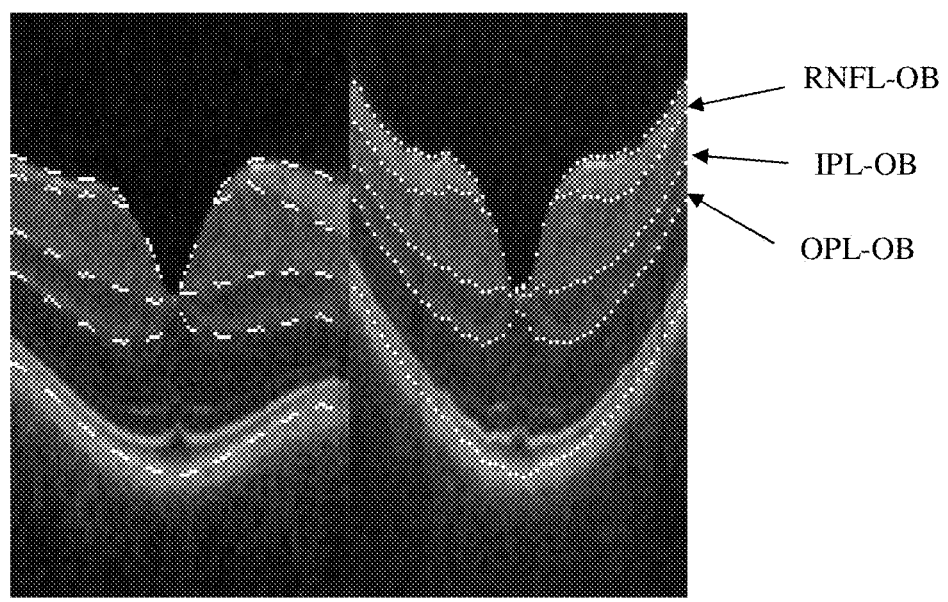
FIG. 4 shows segmented fast (left) and slow (right) B-scans through the fovea of a patient's eye.

The resulting segmentation identifies the outer boundary of the RNFL (RNFL–OB), the outer boundary of the inner plexiform layer (IPL–OB) and the outer boundary of the outer plexiform layer (OPL–OB). The boundaries are shown in FIG. 4, which shows a fast B-scan through the fovea of the patient on the left and slow B-scan extracted through the fovea of the patient on the right. Using this information it is possible to create thickness maps of the various layers or combinations of layers. The GCL+IPL thickness will be defined as the difference, in micrometers, between the RNFL–OB and the IPL–OB boundaries. In the image data, the boundary between these two layers is indistinct so that they are difficult to distinguish from each other, but the combined thickness is considered to be indicative of the health of RGCs.

Using the thickness maps, it is possible to derive metrics to support the clinician's management of the patient. Possible representative values that could be determined include the average thickness about a specific annulus, a minimum thickness for a specific sector, quadrant clock-hour or meridian of the annulus, or super-pixel values whereby the thickness at a certain number of pixels (super-pixel) is displayed. In each case the representative value could be displayed alone or with its corresponding location on a thickness map. Additionally a comparison of the representative value relative to the distribution of thicknesses in a collection of data from a normal population could be displayed or stored.

Figure 5:
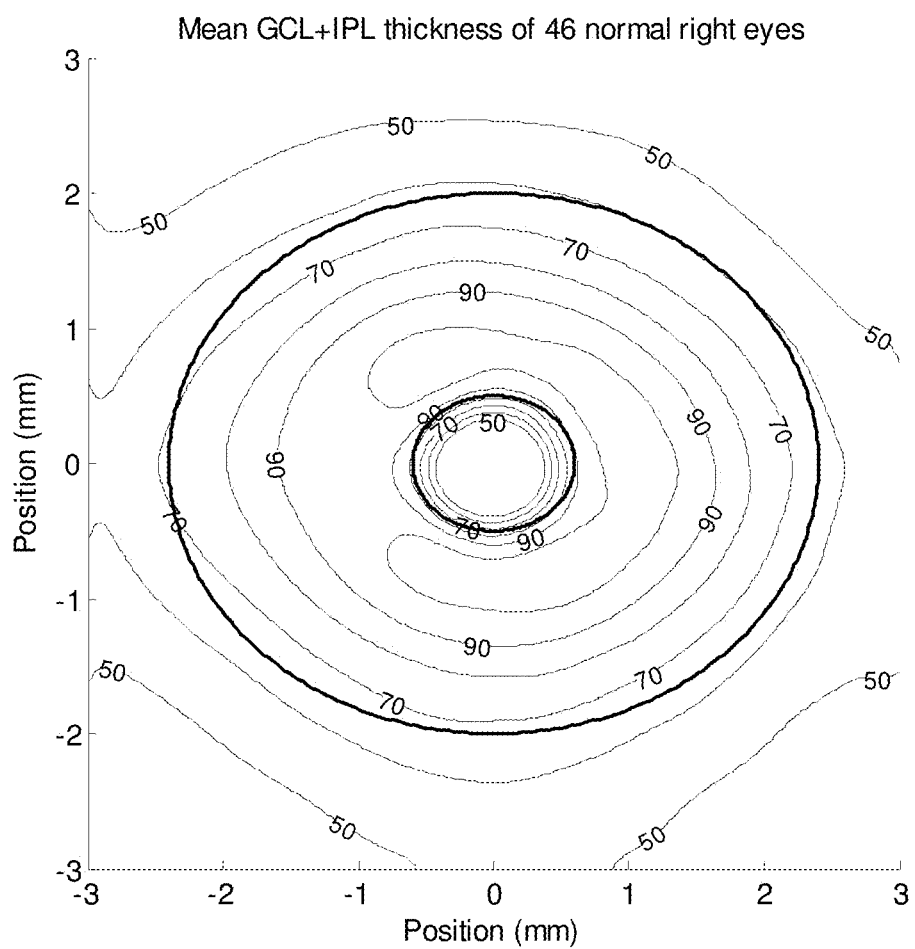
FIG. 5 shows the mean GCL+IPL thickness for 46 normal right eyes.

The preferred embodiment computes average subfield thicknesses within an annular region. The thickness can be computed between individual layers or two selected layers (IPL–OB minus RNFL–OB) to represent the GCL+IPL. The invention described herein uses elliptical annuluses centered on the fovea. Ellipses are the simplest geometry that approximates anatomy, but other shapes or geometries could be used. FIG. 5 shows a contour map of the average GCL+IPL thickness from 46 normal right eyes. The fovea of each eye was centered on the origin before averaging. The contour interval is 10 micrometers, with every other contour labeled. An elliptical annulus is superimposed (heavy lines) to show the approximate correspondence between the annulus and the anatomy of the macular GCL+IPL. The specific elliptical annulus used in the analysis has an inner vertical radius of 0.5 mm and an outer vertical radius of 2 mm. The inner horizontal radius is 0.6 mm and the outer vertical radius is 2.4 mm (a horizontal stretch of 20%). The size of both the inner and outer rings were selected to exclude areas where the ganglion cell layer is thin and difficult to detect, whereas the amount of stretching in the horizontal direction was selected in an effort to conform closely to the observed distribution of the ganglion cell layer in a normal eye. The size corresponds roughly to contour lines of the GCL+IPL thickness of the mean normal as illustrated in FIG. 5. Different dimensions for the elliptical axes are also possible.

Figure 6:
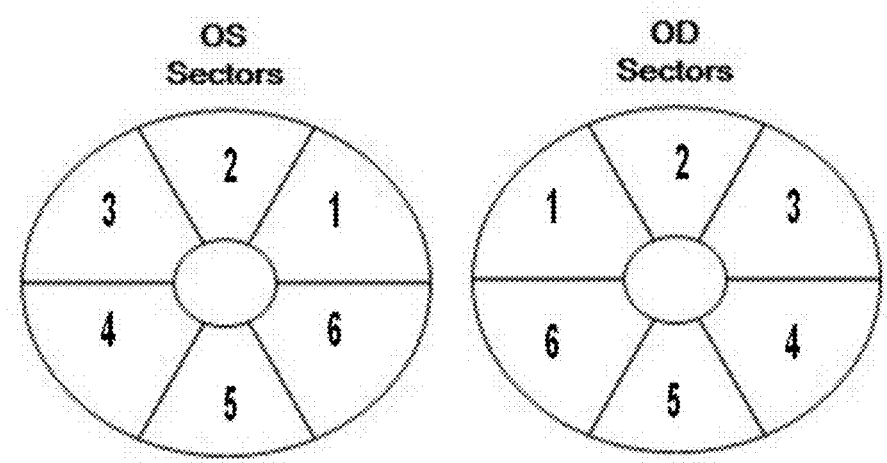
FIG. 6 shows elliptical annuluses for the left and right eyes divided into six equal sectors for analysis purposes.

FIG. 6 illustrates one set of elliptical annuluses and sectors used for analysis for both left and right eyes. The annular region in FIG. 6 is subdivided equally into six sectors, three in the upper hemifield, and three in the lower. Any configuration of sectors could be used in the analysis. The methods described here align the sectors to the temporal raphe to respect the known anatomy of ganglion cell damage in glaucoma. If an odd number of sectors is chosen, it would be desirable to configure them such that a horizontal division between two sectors falls on the temporal raphe. In this case the nasal sector would be left out of any hemifield analysis. While the analysis pattern disclosed here is based on anatomy to select regions of uniform thicknesses, sector patterns based on patterns of tissue loss can also be imagined.

Using calculation of the average GCL+IPL thickness within the annulus, the minimum thickness can be determined, where the minimum is defined as the minimum of the average GCL+IPL thickness along all possible meridians that go from the inner ellipse to the outer ellipse. If a series of radial spokes is defined, each spoke has an average GCL+IPL thickness, and the average thickness of the spoke with the smallest value for that average is reported as the minimum. The direction of the spoke with the smallest value can also be reported. Additional ways to define the minimum can be imagined including widening the lines into wedges or establishing a series of concentric elliptical annuluses. The minimum is a useful "overall abnormality assessment" because an elliptical annulus centered on the fovea defines a region that in normals has uniform average thickness as a function of azimuth. Damage upsets this uniformity to produce a meaningful (in size and location) change in the minimum. Selecting the minimum from the set of maximum values along the radial spokes would be another way to identify damage. Since the maximum would trace the thickest part of the ganglion cell layer as the measurement moves around the fovea, any impact of disease should show up in such a measurement. Any set of regions defined to be roughly non-variant as a function of location would also be useful for detecting disease. Another way to use an extremum in the measurement to detect disease would be to look for a maximum deviation from the expected normal value.

In Cartesian coordinates, a thickness value within the elliptical annulus is defined by determining if the thickness value position (x, y) is located between two ellipses as follows:

$$\frac{(x-x_0)^2}{a_i^2} + \frac{(y-y_0)^2}{b_i^2} >= 1$$

and $$\frac{(x-x_0)^2}{a_o^2} + \frac{(y-y_0)^2}{b_o^2} <= 1$$

where $(x_0, y_0)$ is the fovea location, $(a_i, b_i)$ represent the inner horizontal and vertical ellipse semiaxes, and $(a_o, b_o)$ represent the outer horizontal and vertical semiaxes. Each subfield sector is defined as a region bounded between two radial lines intersecting the fovea location $(x_0, y_0)$.

While Cartesian coordinates have been used up to this point, a useful framework for carrying out the analysis involves polar coordinates. TSNIT plots around the optic disc are familiar to the clinician, but they represent just a single value along a circle (or sometimes the average value on a thin annulus) and do not incorporate analysis along the radial direction. The method described here preserves the thickness information for the chosen radius around all angles. Letting $-180°<\theta<+180°$ and aligning $\pm180°$ with the temporal raphe respects the known pattern of ganglion cell damage in glaucoma, as already recognized in the well-known hemifield defect (nasal step) in visual fields.

Figure 7:
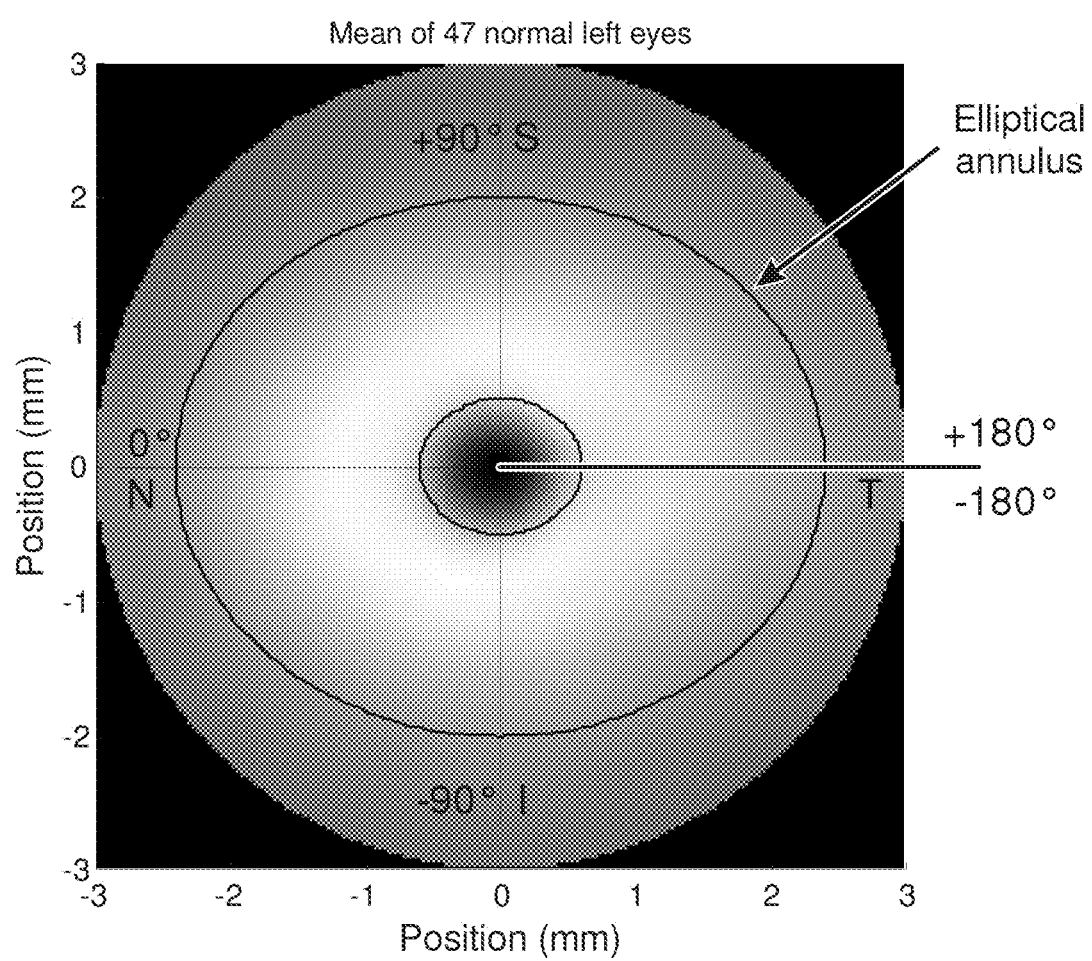
FIG. 7 shows an elliptical annulus superimposed on a thickness map displaying the mean of 47 normal left eyes in Cartesian coordinates.

FIG. 7 shows a map of the normal GCL+IPL thickness in Cartesian coordinates. The elliptical annulus used for the various analyses has been superimposed. The orientation of a polar coordinate system that respects the anatomy of the temporal raphe is depicted as a line at $\pm180°$. The mean GCL+IPL thickness of 47 normal left eyes is centered on the origin and cropped at a radius of 3 mm Left eyes were chosen for this illustration because the $\pm180°$ meridian is not in the customary position, thus emphasizing that the coordinate system respects anatomy.

Figure 8:
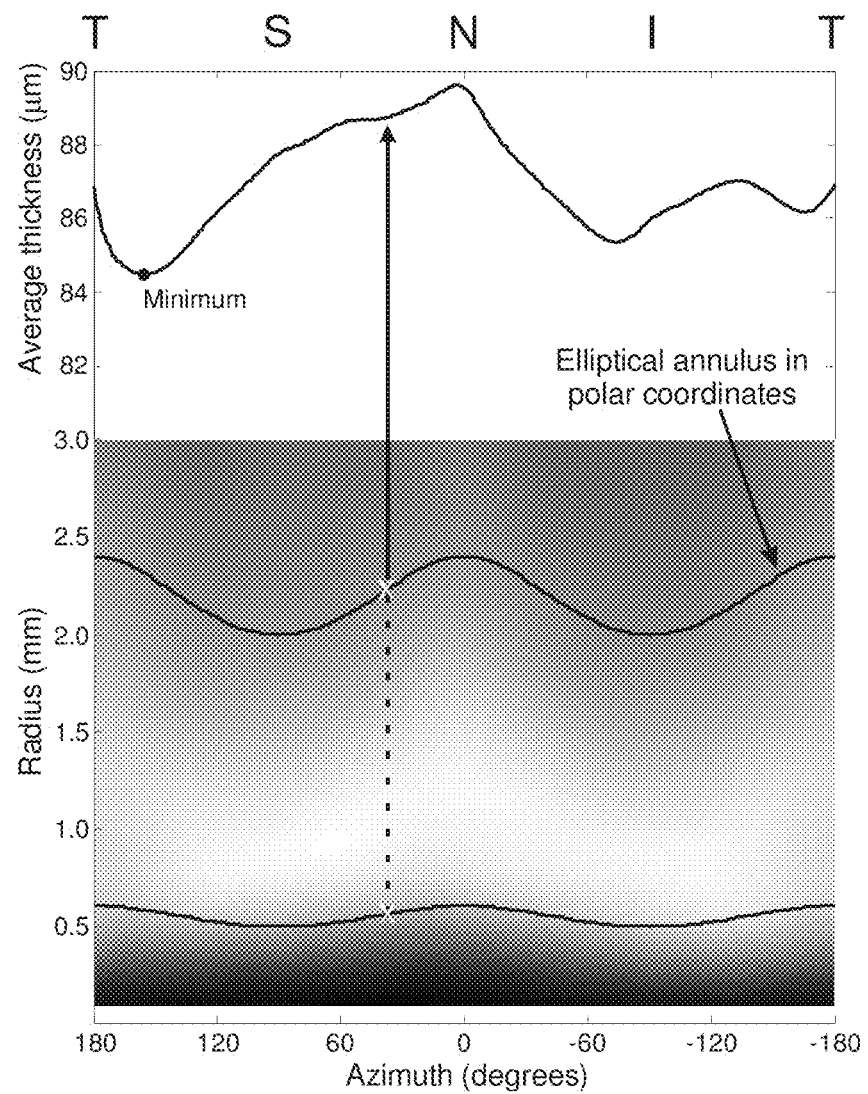
FIG. 8 shows the thickness map and elliptical annulus of FIG. 7 transformed into polar coordinates.

FIG. 8 shows the transformation of the Cartesian GCL+IPL map in FIG. 7 to polar coordinates. The polar form of the equation for an ellipse with major axis a along the x-axis and minor axis b along the y-axis is $$r(\theta) = \frac{ab}{\sqrt{(b\cos\theta)^2 + (a\sin\theta)^2}}.$$

This equation is used to draw the elliptical annulus on the polar map shown in the bottom panel of FIG. 8. The average thickness for a spoke along a meridian $\theta$ (illustrated as a dashed line between the two X's on the figure) is then easily calculated by integrating the thickness along the radial coordinate according to $t_{avg}(\theta) = \int_{r_1}^{r_0} t(r)dr$, where $r_1(\theta)$ and $r_0(\theta)$ are the inner and outer radii of the annulus at meridian $\theta$. For discrete data the integrals can be approximated by summations. The thicknesses by angle are shown in the top panel of FIG. 8 and the minimum value is found. The average thickness for these 47 normals varies by less than 6 micrometers around the fovea, emphasizing the value of the elliptical geometry. Unlike the TSNIT plot used for RNFL, here the cut at T is not arbitrary, but is determined by anatomy.

Additionally, it is also possible to weight the average to give special emphasis to diagnostically important regions (determined empirically), so the average would be $\int Tw(r,\theta)dr/\int w(r,\theta)dr$, where $w(r,\theta)$ is the desired weighting function. Then, for example, if loss usually occurs first at the peak thickness, sensitivity can be increased there.

Once the desired representative value has been determined, in this example, the minimum thickness, it is desirable to compare the value to a collection of measurements from a normal population to assess the overall abnormality of the patient and track disease progression over time. Adjustment of normative data collected on the RNFL layer was described in U.S. Pat. No. 7,798,647 hereby incorporated by reference. This patent describes a method to reduce variability in a collection of nerve fiber measurements using anatomical or anatomical contextual information. This improves specificity or sensitivity of the comparison of normative data to measurements. The normal limits used for comparison for RNFL data are adjusted according to age in order to account for expected age-related loss of RNFL, and this is also desirable for ganglion cell analysis. Additionally, the following methods remove interindividual variability unique to the macular region of the eye as part of the analysis. While the examples used herein compare the measurements to a database derived from measurements of healthy or normal eyes, it may also be beneficial to compare the measurements to a database derived form measurements of abnormal eyes.

Prior to comparison, it is desirable to develop a canonical form, in this case a Standard Macula, that characterizes the normal GCL+IPL. The ideal canonical form is a surface in two dimensions that, when suitably transformed, will match with some deviation the thickness map of a macular layer from a healthy eye while minimizing the deviation over a set of maps from healthy eyes. FIG. 5, FIG. 7 and FIG. 8 taken together show anatomical features common to the GCL+IPL of normal maculas that allow the development of a canonical form for the normative data. A basic canonical form will possess approximately elliptical symmetry with a division along the temporal raphe. The layer thickness will increase from zero at the fovea to a maximum and then decline toward the periphery to form an annulus. Polar coordinates with the center at the fovea and extending from −180° to +180° along the temporal raphe provide a convenient system for analysis and Cartesian coordinates are natural for display, but analyses can be carried out in either system. Although a pure GCL map is ideal, as above, this analysis is applied to the GCL+IPL layer, but could potentially apply equally to other layers or combinations of layers in the macular region of the eye. A reasonable estimate for the canonical form of the macular GCL+IPL can be obtained from the mean of GCL+IPL maps from a population of normal eyes, as shown in FIG. 7 for 47 normal left eyes. Other estimates of an optimal canonical form can be imagined and improvements to a basic canonical form will be discussed in detail below.

The starting point for the development of a canonical form, or Standard Macula, presented here is a collection of GCL+IPL thickness maps for both the right and left eyes from a population of normal subjects. The first step, for the right and left eyes separately, involves aligning all the maps on their foveas. In polar coordinates this can be accomplished by converting each map to polar coordinates centered on the fovea, with the ±180° axis aligned with the temporal raphe and +90° superior. Thus, the 0° meridian will extend nasally (right in a RE and left in a LE). In Cartesian coordinates this can be accomplished by translating each map so the fovea falls at the origin. In the second step the mean of the aligned GCL+IPL thickness maps is calculated at each data point to form a map of the mean as shown in FIG. 7. This map then serves as a Standard Macula that can be characterized with measures that can guide the transformation of an individual map to the canonical form, or vice versa. The two measures used in the example that follows are the average diameter of the foveal depression and the average GCL+IPL thickness over a specified area. Other methods to obtain and improve a canonical form and other measures to characterize a canonical form can also be imagined One such idea would be creating a canonical form based on a model of the macula characterized by parameters rather than empirical data.

The use of a canonical form can reduce the interindividual variability within the normative data prior to comparison with data from a patient. Two methods for accomplishing this are presented here: 1) fovea correction, wherein variations in the size of the fovea among subjects are accounted for by applying a radial transformation to the individual maps and 2) thickness variation reduction in which variations due to local deviation from the canonical form are isolated by applying an axial transformation to an individual map so that it has the same average thickness as the Standard Macula. These two methods can be applied alone or in combination to a collection of normative data. The steps involved in one approach may be understood by referring to the flow chart in FIG. 9, where the two methods are applied in succession. Additional transformations to characterize and fit the canonical form can be imagined and the teaching here is intended to cover the concept of using spatial transformations of retinal structures in general to improve the fit to a canonical form.

Figure 9:
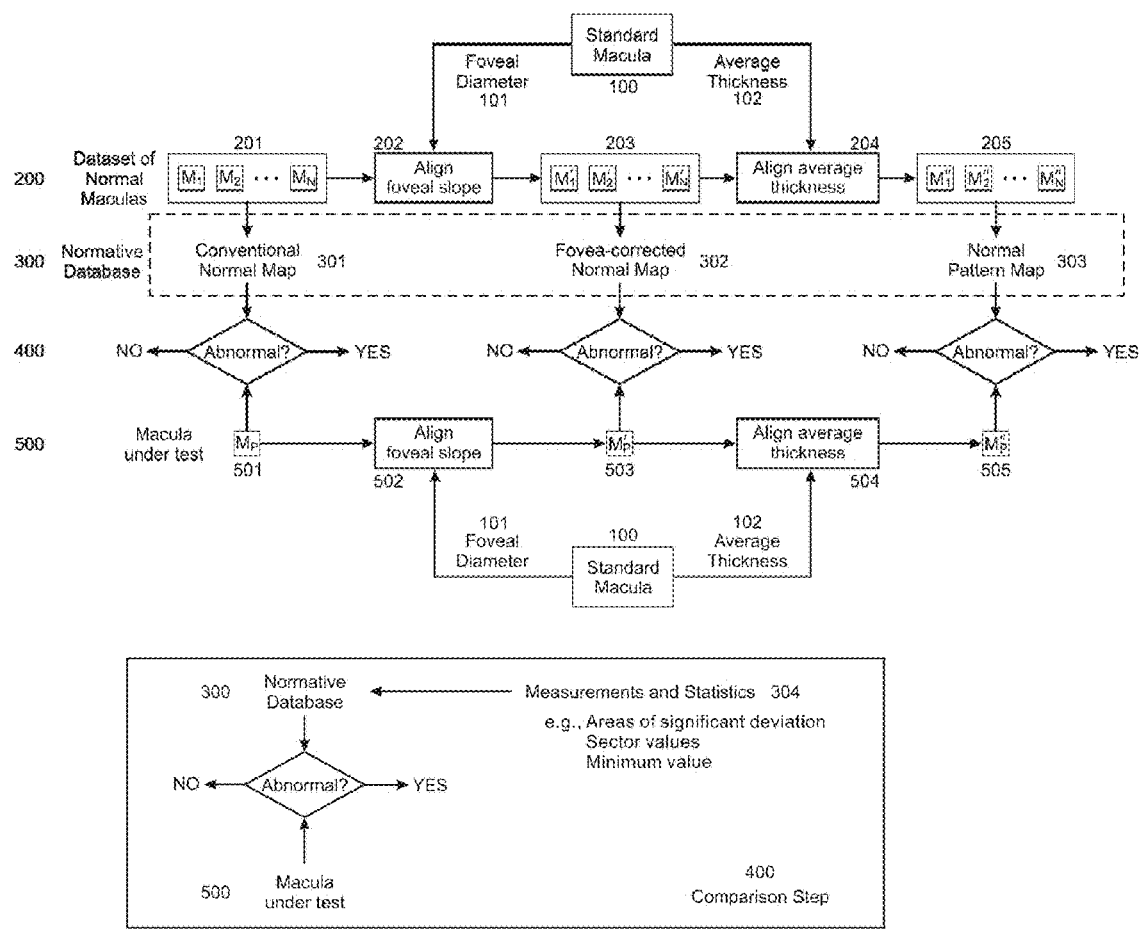
FIG. 9 shows a flow chart of the steps used to form a normative database from a collection of normal data and the steps used to compare a GCL+IPL map to the normative database.

FIG. 9 illustrates one approach to use the concepts of this invention. The concepts are used first to form a normative database 300 from a collection of normal data 200 and then in a comparison step 400 are used to determine whether abnormality is exhibited by a macula to be tested 500.

A normative database 300 is formed from a collection of thickness maps $M_1 \ldots M_N$ 201 obtained from a dataset of normal maculas 200. The normative database 300 consists of a Conventional Normal Map 301, a Fovea-corrected Normal Map 302 and a Normal Pattern Map 303. These maps and associated measurements and statistics 304 are derived from $M_1 \ldots M_N$ 201 and two collections of transformed maps $M'_1 \ldots M'_N$ 203 derived from $M_1 \ldots M_N$ 201 and $M''_1 \ldots M''_N$ 205 derived from $M'_1 \ldots M'_N$ 203. In the first transformation step 202 each member of 201 is radially shifted to align its foveal diameter to the foveal diameter 101 of the Standard Macula 100 and produce the first collection of transformed maps $M'_1 \ldots M'_N$ 203. In the second transformation step 204 each member of $M'_1 \ldots M'_N$ 203 is axially shifted to align its average thickness to the average thickness 102 of the Standard Macula 100 and produce the second collection of transformed maps $M''_1 \ldots M''_N \ldots M''_N$ 205. The Conventional Normal Map 301 is formed from the mean and variance of $M_1 \ldots M_N$ 201, the Fovea-corrected Normal Map 302 is formed from the mean and variance of $M'_1 \ldots M'_N$ 203 and the Pattern Normal Map 303 is formed from the mean and variance of $M''_1 \ldots M''_N$ 205. The normative database 300 also includes measurements and statistics 304 that characterize the three collections of maps.

A macula to be tested 500 is scanned to produce an original map $M_P$ 501, which is transformed by radial shifting 502 to align its foveal diameter with the foveal diameter 101 of the Standard Macula 100 to produce a map $M'_P$ 503, which is transformed by axial shifting 504 to align its average thickness with the average thickness 102 of the Standard Macula 100 to produce a map $M_{P''}$ 505.

Comparison steps 400 to determine whether the macula to be tested 500 exhibits abnormality may be carried out between $M_P$ 501 and the Conventional Normal Map 301, $M'_P$ 503 and the Fovea-corrected Normal Map 302, or $M_{P''}$ 505 and the Pattern Normal Map 303. A comparison step may use measurements and statistics 304 from the normative database 300 in order to identify, for example, areas of significant thickness deviation or aberrant values of sector thickness or minimum thickness.

Figure 10:
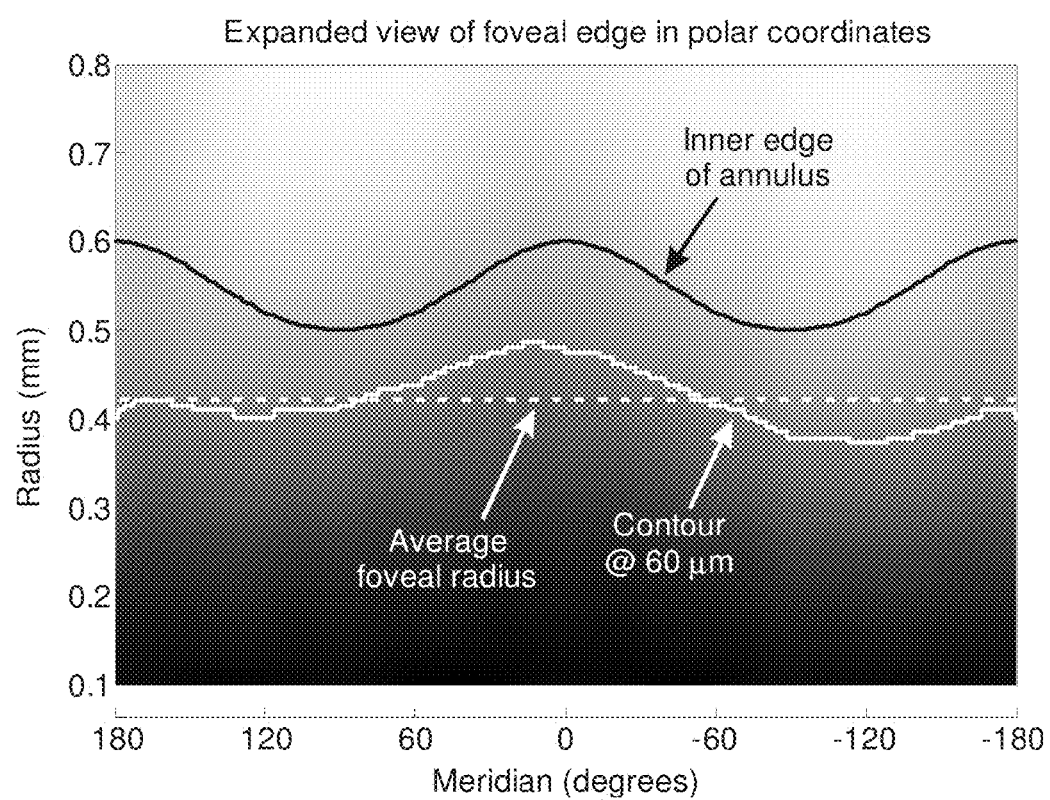
FIG. 10 shows the inner edge of the GCL+IPL Standard Macula in polar coordinates shown with an expanded view of the foveal slope.

Variation in the size of the foveal depression and the surrounding mound of ganglion cell bodies depends on gender, ocular pigmentation and other demographic variables (see for example Wagner-Schuman, et al., "Race and sex-related differences in retinal thickness and foveal pit morphology IOVS", 52:624-634, 2011), and demographic stratification can be used to reduce some of this variation, but the following method can reduce the variation without regard to demographics. This method is described in terms of polar coordinates. First each map is converted to polar coordinates centered on the fovea with the ±180° axis aligned with the temporal raphe and +90° superior. Thus, the 0° meridian will extend nasally (right in a RE and left in a LE) as shown in FIG. 7. For each map and for the Standard Macula previously determined, determine a measure of the size (width) of the foveal depression. There are many ways this could be done, e.g., fitting a paraboloid to the depression (see Giovanni Gregori et al., "The Geometry of the Normal Fovea" ARVO 2010 Program #270 Poster #D623). The inner edge of the GCL+IPL Standard Macula in polar coordinates is shown with an expanded view of the foveal slope in FIG. 10. Here a canonical form is approximated by the mean of 47 normal left eyes. The size of the foveal depression, determined as the average diameter of the contour line at a thickness of 60 micrometers, is 0.85 mm for this dataset. Then a radial transformation can be applied to each map to match the sizes of the foveal depressions between an individual map and the Standard Macula. One such radial transformation is a shifting to align the slopes of the foveal depressions to the foveal slope of the Standard Macula. This radial transformation is easily applied with polar coordinates. Additional possible radial transformations can be imagined including radially scaling the measurements.

Figure 11:
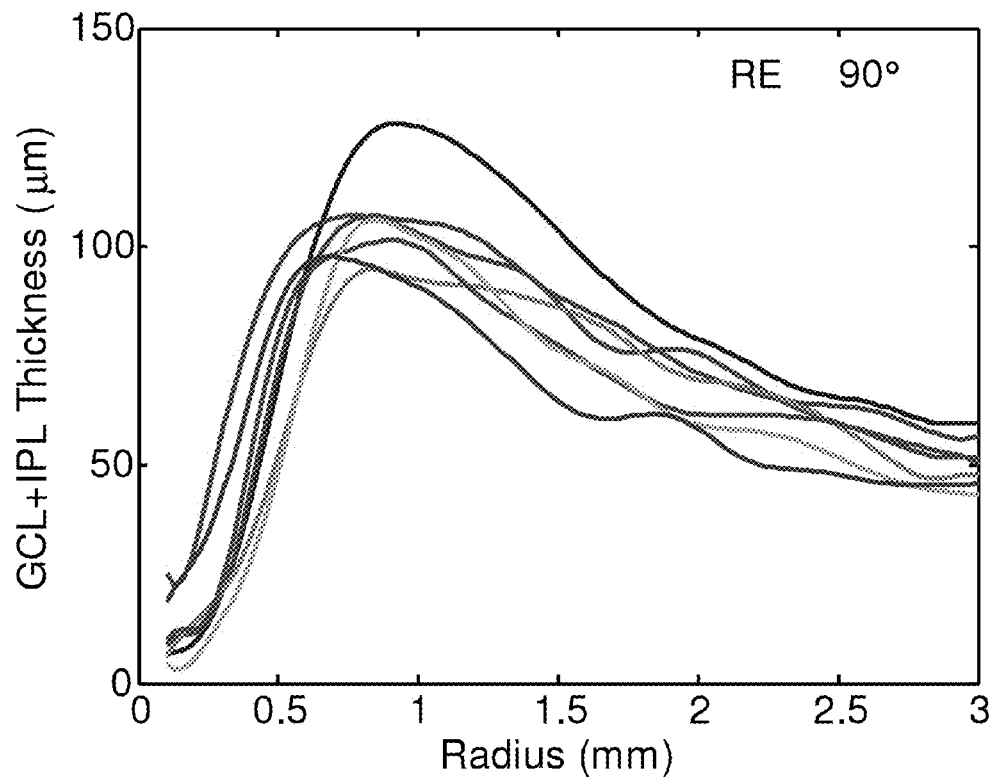
FIG. 11 shows the vertical GCL+IPL thickness profiles from seven normal right eyes.
Figure 12:
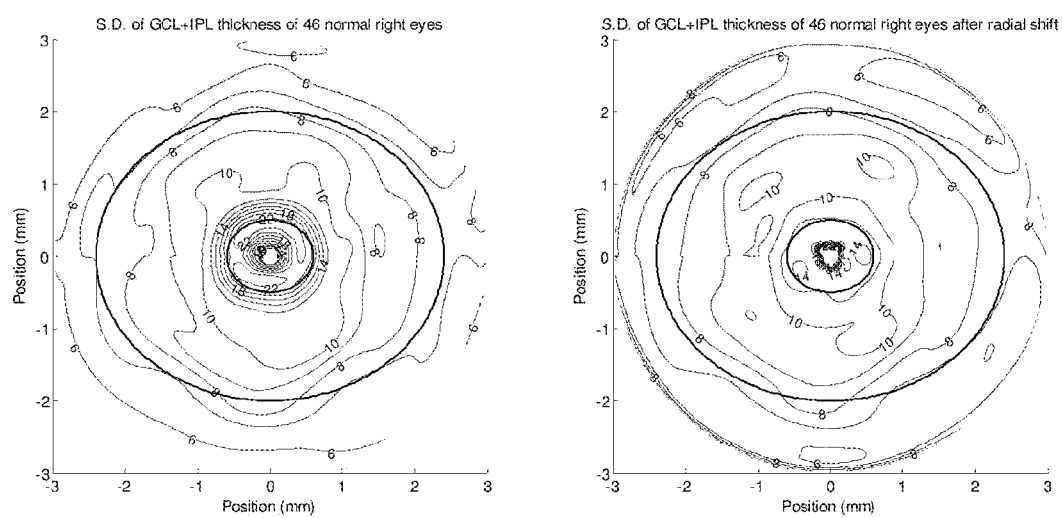
FIG. 12 shows the result of the radial transformation applied to correct for variations in foveal size among individuals.

The radial transformation described in detail here is a radial translation (shifting), because it aligns the rising edges of foveas that have the same slope. This is illustrated for the vertical GCL+IPL thickness profiles from seven normal right eyes in FIG. 11. The seven eyes were chosen to represent quantiles in overall thickness from a population of 46 normal right eyes. Thus, the lowest profile is from the eye with the thinnest GCL+IPL, the highest is from the thickest and the other five profiles include the central 67% of the population. Each profile extends radially upward (+90°) from the fovea; all have nearly parallel leading edges. Radial shifting preserves the shape of the extrafoveal GCL+IPL; the entire GCL+IPL simply moves toward or away from the fovea. To perform radial shifting in polar coordinates for each map, one-half the difference between the widths of the fovea from the Standard Macula and the fovea of the given map is simply added to all radii. FIG. 12 shows the results of such a transformation on a population of healthy right eyes. An elliptical annulus is superimposed for reference to other figures. The left panel shows a contour map of the standard deviation (s.d.) of GCL+IPL thickness from a population of healthy right eyes with foveas centered on the origin. The s.d. increases markedly near the edge of the foveal depression as a consequence of interindividual differences in foveal size. The right panel shows a contour map from the same eyes corrected for foveal size by radial shifting to match the foveal size of a Standard Macula as described above (Fovea Corrected Normal Map). The s.d. near the fovea has decreased considerably. In both figures the contour interval is 1 micrometer for s.d.

<10 micrometers and 2 micrometers for s.d. >10 micrometers. Only every other contour is labeled for clarity. As will be seen in more detail later, a suitably transformed patient map can be compared to the Fovea-Corrected Normal Map to determine if there has been loss of GCL thickness relative to the normal population.

The preceding description of foveal correction as a means to transform an individual map to a canonical form is a specific example of a general approach to the reduction of interindividual variability. This approach is to identify and measure a structural feature of the canonical form, measure the same feature in the individual map, and then suitably transform the individual map to make it congruent with the canonical form (or vice versa). A second example of a structural feature that could be radially transformed in the manner described above is the perifoveal ridge of high ganglion cell density that dominates the normal GCL+IPL map. The perifoveal ridge approximates a horizontally oriented ellipse in all eyes, but the size of the ellipse differs among eyes. The size of the perifoveal ridge can be measured as its average radius in polar coordinates and radial shifting applied as described for the foveal depression. The sizes of the perifoveal ridge and foveal depression are positively correlated (Knighton "The Shape of the Normal Human Ganglion Cell and Inner Plexiform Layers and its Application to Glaucoma" in preparation), so this transformation will not only align the perifoveal ridge with the Standard Macula, but will also tend to align the foveal edges.

The second method for reducing interindividual variation among a collection of normative data is to apply a thickness transformation to an individual map so that it has the same average thickness as the Standard Macula. Removal of overall thickness variation emphasizes local deviation from normal. Use of a Pattern Map has been proposed by others (see for example US Patent publication 2008/0309881; Tan, et al., Ophthalmology 116:2305-2314, 2009), but they use scaling (normalization) to transform GCL thickness and express loss as a percentage, which is difficult to interpret anatomically. The transformation used in this invention is axial shifting, which preserves the absolute size of local deviations. This has two advantages: 1) depressions in an unusually thick GCL are not reduced in size, as they are by normalization, making them easier to detect, and 2) the size of deviations from the Pattern Map will be proportional to ganglion cell loss, the fundamental anatomical lesion in glaucoma, aiding interpretation. The Pattern Map concept can be applied in either polar coordinates or foveally-aligned Cartesian coordinates. As mentioned, the Pattern Map concept can be applied either to the dataset of fovea-corrected maps ($M'_1 \ldots M'_N$ in FIG. 9) or to the original collection of measurements ($M_1 \ldots M_N$).

Figure 13:
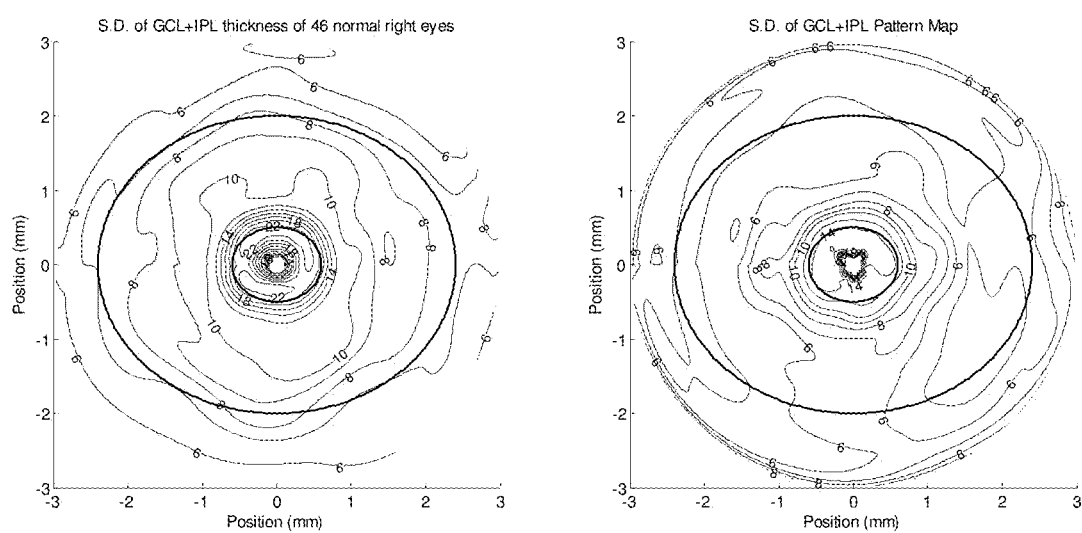
FIG. 13 shows the result of the axial transformation applied to account for variations in thickness among individuals.

The axial shifting method is carried out on a set of normal maps as follows. For each map and the Standard Macula a measure of the average thickness of the GCL+IPL (height of the map) is determined. This could be the average thickness over an elliptical annulus as previously described. Each map is then axially shifted by the difference between its average thickness and the average thickness of the Standard Macula. The result of this step is a normative Pattern Map for the GCL+IPL without the thickness variation due to differences between individuals; the only variation is due to individual deviations from the Standard Macula. As shown in more detail later, a suitably transformed patient map can be compared to the Pattern Map to identify regions of significant local loss. The ideal Pattern Map is identical to the canonical form for GCL+IPL. FIG. 13 shows the results of the axial transformation for the same collection of normative data as FIG. 12. Each GCL+IPL thickness map was first corrected for foveal size, as described for FIG. 12, then the average thickness within the elliptical annulus was calculated for each map. Each map was then shifted in the axial direction (thickness) by the difference between its average and the average thickness of the Standard Macula. The mean of this axially-shifted dataset closely approximates the Standard Macula, but its standard deviation, which no longer includes overall interindividual variation, is smaller than that of either the original dataset (FIG. 13, left panel) or the Fovea-Corrected Normal Map (FIG. 12, right panel).

Figure 14:
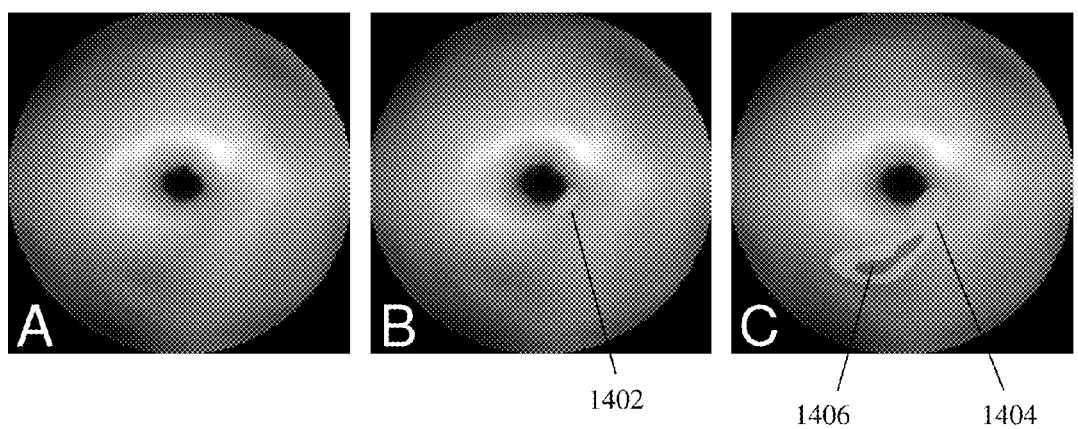
FIG. 14 shows a GCL+IPL map from a patient that is tested against a normative database.

In order to determine how a GCL+IPL map from a patient's eye under examination, referred to as a test map, differs from normal, the following procedure can be implemented. FIG. 14 illustrates the procedure with an example from the left eye of a patient suspected of having mild glaucomatous damage. This eye has thicker than average GCL+IPL thickness and a smaller than average foveal diameter. The lighter areas 1402 in FIG. 14B and 1404 in FIG. 14C indicate deviations greater than 2 s.d. below normal and the darker area 1406 in FIG. 14C indicate deviations greater than 3 s.d. below normal. The following assumes that both the Fovea-Corrected Normal Map and the Pattern Map have the canonical form; they only differ in variance. The analysis is carried out in polar coordinates. First the test map is compared to the mean and variance of the original normative dataset prior to any shifting. If the test map differs greatly (e.g., 3 s.d. below normal over a large enough area), no further comparison is needed; the test map has been identified as abnormal. Performing this initial comparison will screen out eyes that are so badly damaged that a selected measure of foveal size is erroneous. In the example, FIG. 14A shows no deviation of the test map from the unshifted normal map.

Secondly, the foveal size of the test map is measured and the radial shift (or other radial transformation) is applied to align it with the Fovea-Corrected Normal Map. The desired statistical comparisons using the lower variance of the Fovea-Corrected Normal Map can then be carried out. FIG. 14B shows radial shifting applied to the test map of the example before the comparison. Note that, compared to FIG. 14A, radial shifting causes the foveal depression to appear larger. In this step the reduced variance of the Fovea-Corrected Normal Map reveals a small abnormal area on the foveal slope of the test map (patch 1402 adjacent to the foveal depression).

Finally, the GCL+IPL thickness of the test map is measured and the axial shift needed to align it with the Pattern Map is applied. This should reveal local areas of the test map that differ from the Pattern Map by statistically determined amounts, i.e., areas of local deviation. The preferred shift would be of the Pattern Map to the thickness of the test map, so that areas of deviation can be displayed on the test map. If the Pattern Map is formed from the Fovea-Corrected Normal Map, it must be radially-transformed to the foveal size of the test map before comparison. FIG. 14C shows the result of this comparison for the example. Axial shifting of the patient's map to match the average thickness of the Standard Macula reveals an arcuate region that deviates significantly from the normal pattern, strongly suggesting the presence of glaucomatous damage.

It will be apparent that although the flow chart in FIG. 9 shows transformations applied to data to align them with a Standard Macula, the same analytical effect can be carried out by transforming a Standard Macula to align it with data. Indeed, in a typical application combinations of transformations in one direction or the other may prove to be most advantageous for analysis and display.

An additional embodiment of the present invention's use of axial shifting to produce the Pattern Map lends itself to a Hemifield Test. Rather than shifting by the difference in averages over the entire elliptical annulus, the average thickness of the thicker hemifield (or a sub-region located in a hemifield) can be used to align the thicker hemifield with the corresponding hemifield of the Pattern Map. A metric for the affected hemifield or subregion is then the average depth below normal over a standard area, which will be proportional to the number of missing ganglion cells in the more affected hemifield relative to the "normal" hemifield.

The methods described above are specific examples of the more general concept of using additional information to account for and reduce the variance in a normative database and improve the detection of glaucomatous damage. In this invention the information is measurements of structural features of the GCL+IPL (or GCL) thickness map. Rather than being used to guide spatial transformation, as described above, this information could also be used as extra input variables in statistical analyses to discriminate normal from glaucomatous eyes.

The methods described above are intended to be carried out automatically via a processor attached to an imaging system but could be performed manually. The analysis could be carried out during data collection or could be stored and recalled for subsequent analysis. Data from various stages of the analysis could be stored and later recalled for comparison. Although various embodiments that incorporate the teachings of the present invention have been shown and described in detail herein, those skilled in the art can readily devise other varied embodiments such as different canonical representations or transformations to reduce the variance of a normative database that still incorporate these teachings.

The following references are hereby incorporated by reference:

U.S. PATENT DOCUMENTS

U.S. Patent Publication No. 2008/0309881 Huang et al. "Pattern Analysis of Retinal Maps for the Diagnosis of Optic Nerve Diseases by Optical Coherence Tomography".

U.S. Pat. No. 7,347,548 Huang et al. "Method and Apparatus for Measuring a Retinal Sublayer Characteristic".

U.S. Patent Publication No. 2010/0290004 Huang et al. "Characterization of Retinal Parameters by Circular Profile Analysis".

U.S. Patent Publication No. 2010/0290005 Huang et al. "Circular Profile Mapping and Display of Retinal Parameters."

U.S. Pat. No. 7,798,647 Meyer at al. "RNFL Measurement Analysis".

U.S. Pat. No. 7,641,339 Hanagi et al "Ophthalmologic information processing apparatus and ophthalmologic examination apparatus"

US Patent Publication No. 2009/0033868 Huang et al "Characterization of the Retinal Nerve Fiber Layer"

OTHER PUBLICATIONS

Leung et al. "Comparison of Macular and Peripapillary Measurements for the Detection of Glaucoma: an Optical Coherence Tomography Study" *Ophthalmology* 2005 March;112(3):391-400.

Choma, M. A. et al. (2003). "Sensitivity Advantage of Swept Source and Fourier Domain Optical Coherence Tomography." *Optics Express* 2003 11(18): 2183-2189.

Ozden-Gurses et al., "Distribution of retinal nerve fiber layer thicknesses using Cirrus™HD–OCT Spectral Domain technology" ARVO 2008 Program #A258, Poster #4632.

Wagner-Schuman, et al., "Race and sex-related differences in retinal thickness and foveal pit morphology" *Invest Ophthalmol Vis Sci* 52:624-634, 2011.

Giovanni Gregori et al., "The Geometry of the Normal Fovea" ARVO 2010 Program #270 Poster #D623.

Tan, et al., "Detection of Macular Ganglion Cell loss in glaucoma by fourier-domain optical coherence tomography" *Ophthalmology* 116:2305-2314, 2009.

Wang, M et al. "Measurement of local retinal ganglion cell layer thickness in patients with glaucoma using frequency-domain optical coherence tomography" *Arch Ophthalmol* 2009; 127(7):875-881.

Loduca, Ana L. et al. "Thickness Mapping of retinal layers by spectral domain optical coherence tomography" *Am J Ophthalmol* 2010; 150(6): 849-855.

Haeker et al., "Use of Varying Constraints in Optimal 3-D Graph Search for Segmentation of Macular optical Coherence Tomography Images," *MICCAI* 2007 *Presentation* 438.

Zawadzki et al., "Adaptation of a support vector machine algorithm for segmentation and visualization of retinal structures in volumetric optical coherence tomography data sets," *J Biomed Opt.* 2007 ; 12(4)

Mwanza et al., "Profile and Predictors of Normal Ganglion Cell-Inner Plexiform Layer Thickness Measured with Frequency Domain Optical Coherence Tomography" Invest Ophthalmol Vis Sci 1011; 11-7896.

Knighton "The Shape of the Normal Human Ganglion Cell and Inner Plexiform Layers and its Application to Glaucoma" in preparation.

Mwanza Jean-Claude et al "Macular Ganglion Cell-Inner Plexiform Layer: Automated Detection and Thickness Reproducibility with Spectral-Domain Optical Coherence Tomography in Glaucoma" IOVS Papers in Press. Published on Sep. 14, 2011 as manuscript iovs.11-7962.

What is claimed is:

1. A method of assessing the degree of abnormality in a patient's eye based on measurements of the patient's eye obtained with an optical coherence tomography (OCT) device and comparing those measurements to a collection of OCT measurements of eyes of a population of normal subjects, the method comprising:
   creating a standard form of the macula from a collection of measurements contained in a normative database wherein the standard form reduces the inter-individual variability within the normative data, wherein the standard form is created by aligning the collection of measurements to each other and using the mean thickness of the collection of the measurements;
   spatially transforming each measurement in the collection of measurements relative to the standard form based on anatomical information;
   spatially transforming the measurements of the patient's eye relative to the standard form based on anatomical information;
   comparing the spatially transformed measurements of the patient's eye to the spatially transformed collection of measurements to determine the degree of abnormality in a patient's eye; and
   displaying or storing the results of the comparison.

2. A method as recited in claim 1, wherein the collection of measurements are thickness maps of the ganglion cell layer.

3. A method as recited in claim 1, wherein the collection of measurements are thickness maps of the ganglion cell and inner plexiform layers.

4. A method as recited in claim 1, wherein the standard form is created in polar coordinates.

5. A method as recited in claim 1, wherein the spatial transformation involves radially shifting each measurement in the collection relative to the standard form to match the sizes of the foveal depressions.

6. A method as recited in claim 1, wherein the spatial transformation involves radially scaling each measurement in the collection relative to the standard form to match the sizes of the foveal depressions.

7. A method as recited in claim 1, wherein the spatial transformation involves axially shifting each measurement in the collection of measurements based on the average thickness of the measurements and the average thickness of the standard form.

8. A method as recited in claim 1, wherein the spatial transformation involves radially shifting each measurement in the collection relative to the standard form to match the size of the foveal depressions and axially shifting each measurement in the collection of measurements based on the average thickness of the measurements and the average thickness of the standard form.

9. A method as recited in claim 1, wherein the measurements of the patient's eye include measurements of the ganglion cell layer and the inner plexiform layer of a patient's eye.

10. A method as recited in claim 1, wherein the standard form is created using a model representing the macula.

11. A method as recited in claim 1, further comprising displaying the measurements as a function of position relative to the fovea.

12. A method as recited in claim 11, wherein the measurements are displayed using polar coordinates.

* * * * *

UNITED STATES PATENT AND TRADEMARK OFFICE
CERTIFICATE OF CORRECTION

PATENT NO. : 9,775,510 B2
APPLICATION NO. : 14/316548
DATED : October 3, 2017
INVENTOR(S) : Robert W. Knighton et al.

Page 1 of 1

It is certified that error appears in the above-identified patent and that said Letters Patent is hereby corrected as shown below:

In the Specification

In Column 2, Line 2, delete "fast," and insert -- fact, --, therefor.

In Column 3, Line 16, after "macula" insert -- . --.

In Column 9, Line 10, delete "form" and insert -- from --, therefor.

In Column 10, Line 34, delete "$M_N$" and insert -- $M'_N$ --, therefor.

In Column 10, Line 38, delete "$M''_1 \ldots M''_N \ldots M''_N$".

In Column 11, Lines 59-64, delete "<10 micrometers and 2 micrometers for s.d. >10 micrometers. Only every other contour is labeled for clarity. As will be seen in more detail later, a suitably transformed patient map can be compared to the Fovea-Corrected Normal Map to determine if there has been loss of GCL thickness relative to the normal population." and insert the same on Column 11, Line 58, as a continuation of the same paragraph.

Signed and Sealed this
Fifth Day of June, 2018

Andrei Iancu
*Director of the United States Patent and Trademark Office*